(12) United States Patent (10) Patent No.: US 9,289,258 B2
Cohen (45) Date of Patent: Mar. 22, 2016

(54) ABLATION CATHETER SYSTEM WITH SAFETY FEATURES

(75) Inventor: Todd J. Cohen, Port Washington, NY (US)

(73) Assignee: Nexus Control Systems, LLC, Port Washington, NY (US)

( * ) Notice: Subject to any disclaimer, the term of this patent is extended or adjusted under 35 U.S.C. 154(b) by 891 days.

(21) Appl. No.: 13/415,454

(22) Filed: Mar. 8, 2012

(65) Prior Publication Data

US 2012/0232547 A1 Sep. 13, 2012

Related U.S. Application Data

(60) Provisional application No. 61/450,236, filed on Mar. 8, 2011.

(51) Int. Cl.
| | |
|---|---|
| *A61B 18/12* | (2006.01) |
| *A61B 18/14* | (2006.01) |
| *A61B 17/00* | (2006.01) |
| *A61B 18/00* | (2006.01) |

(52) U.S. Cl.
CPC .......... *A61B 18/1492* (2013.01); *A61B 18/1233* (2013.01); *A61B 2017/00203* (2013.01); *A61B 2017/00212* (2013.01); *A61B 2018/00351* (2013.01); *A61B 2018/00708* (2013.01)

(58) Field of Classification Search
CPC ........... A61B 2018/00702; A61B 2018/00898; A61B 2018/00577; A61B 19/22; A61B 2018/00351; A61B 2018/00708; A61B 2018/00904; A61B 2018/0212; A61M 25/0105
USPC .................... 606/20, 32, 34, 41–42
See application file for complete search history.

(56) References Cited

U.S. PATENT DOCUMENTS

| | | | |
|---|---|---|---|
| 5,868,737 A | 2/1999 | Taylor et al. | |
| 5,951,461 A | 9/1999 | Nyo et al. | |
| 6,039,731 A | 3/2000 | Taylor et al. | |
| 6,071,281 A | 6/2000 | Burnside et al. | |
| 6,165,206 A | 12/2000 | Tu | |
| 6,235,022 B1 | 5/2001 | Hallock et al. | |
| 6,808,499 B1 | 10/2004 | Churchill et al. | |
| 6,872,206 B2 * | 3/2005 | Edwards et al. | 606/41 |
| 6,955,674 B2 | 10/2005 | Eick et al. | |
| 7,048,734 B1 | 5/2006 | Fleischman et al. | |
| 7,252,664 B2 * | 8/2007 | Nasab et al. | 606/34 |
| 7,404,720 B1 | 7/2008 | Frey et al. | |
| 7,717,932 B2 | 5/2010 | McFarlin et al. | |
| 7,763,033 B2 | 7/2010 | Gruber et al. | |
| 2006/0079867 A1 | 4/2006 | Berzak et al. | |
| 2007/0233044 A1 | 10/2007 | Wallace et al. | |
| 2008/0245371 A1 | 10/2008 | Gruber | |
| 2009/0149832 A1 | 6/2009 | Sauvageau et al. | |
| 2009/0182325 A1 | 7/2009 | Werneth et al. | |
| 2010/0069734 A1 | 3/2010 | Worley et al. | |
| 2010/0073150 A1 | 3/2010 | Olson et al. | |
| 2010/0312129 A1 | 12/2010 | Schecter | |
| 2011/0172659 A1 | 7/2011 | Brannan | |
| 2011/0190756 A1 | 8/2011 | Venkatachalam et al. | |

* cited by examiner

*Primary Examiner* — Deborah Malamud
(74) *Attorney, Agent, or Firm* — William H. Dippert; Laurence A. Greenberg; Werner H. Stemer

(57) ABSTRACT

A medical system for delivering treatment or therapy to a patient has a kill switch for interrupting the delivery. The kill switch, which can disrupt the delivery directly or can cause an error message to be generated that disrupts the delivery, can be activated by the operator or remotely. In an ablation catheter system, a kill switch mechanism immediately and abruptly terminates delivery of ablation treatment or therapy.

27 Claims, 8 Drawing Sheets

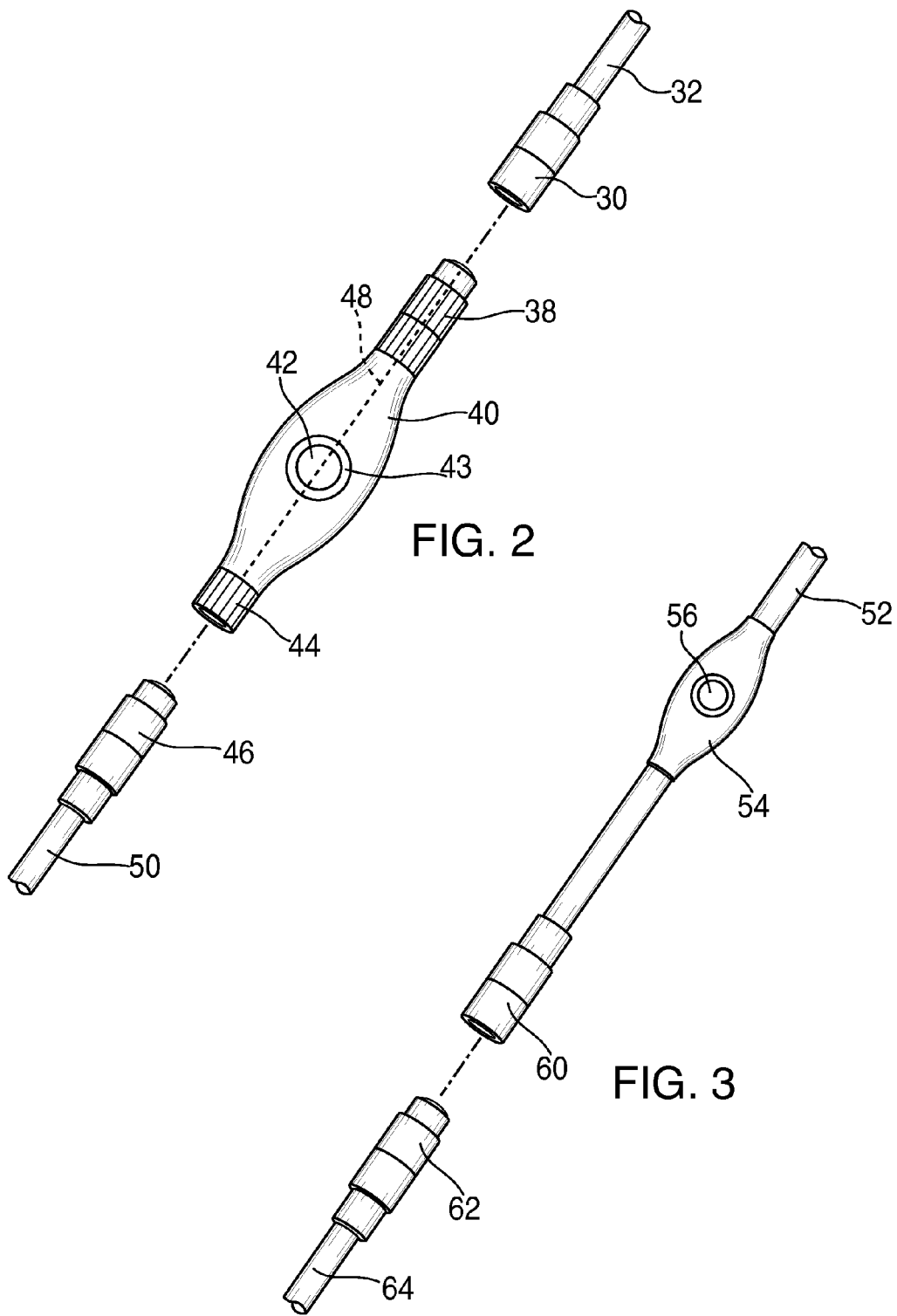

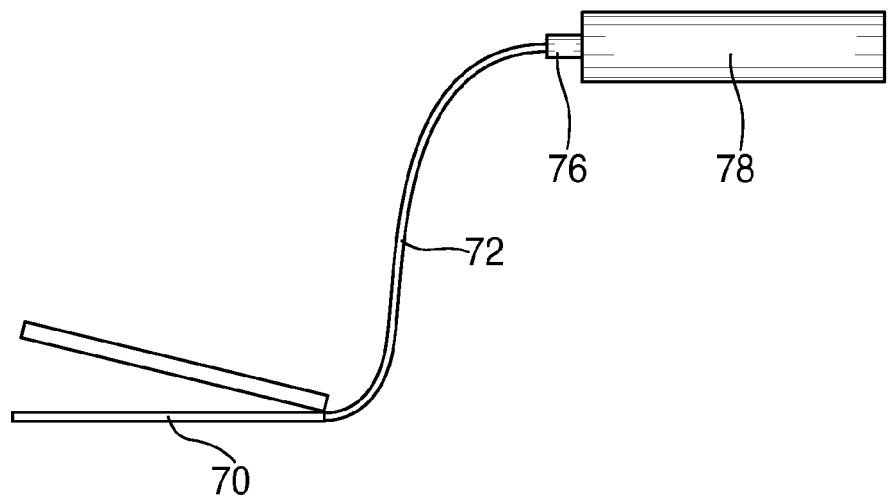
FIG. 4
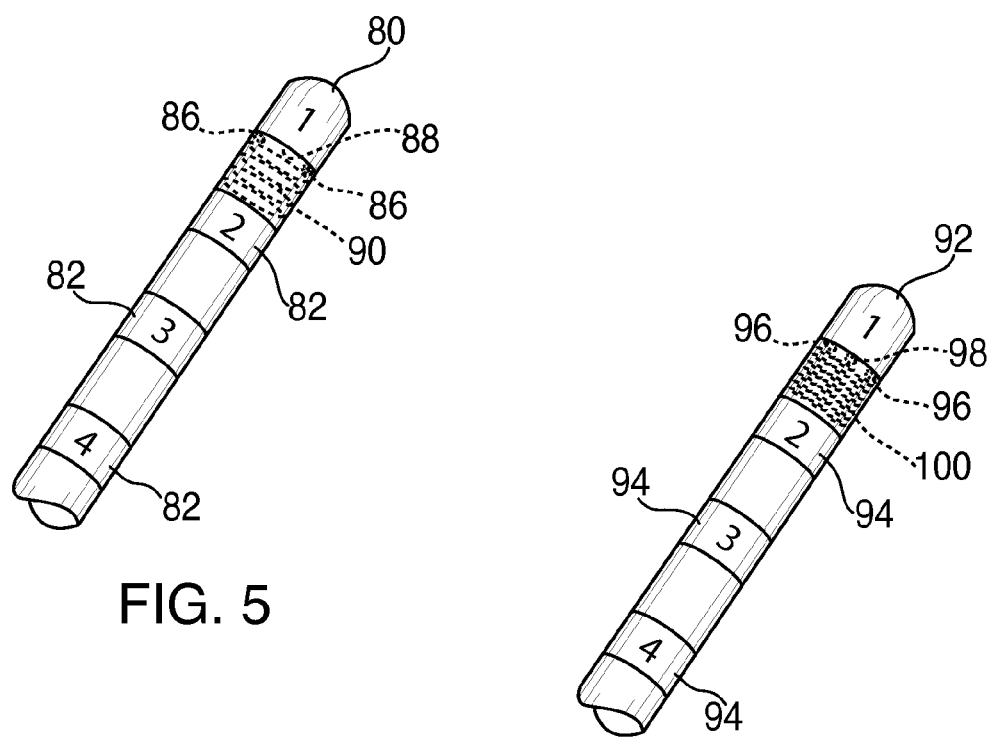
FIG. 5
FIG. 6

ABLATION CATHETER SYSTEM WITH SAFETY FEATURES

CROSS-REFERENCE TO RELATED APPLICATION

This patent application is based upon and claims the benefit of the priority of the filing date of, commonly assigned U.S. Patent Application Ser. No. 61/450,236, filed Mar. 8, 2011, which application is incorporated herein in its entirety.

FIELD OF INVENTION

The present invention relates generally to systems, catheters, and methods for performing targeted tissue ablation in a subject. More particularly, the present invention provides an ablation system having a quick cut-off mechanism.

BACKGROUND OF THE INVENTION

Tissue ablation is used in numerous medical procedures to treat a patient. Ablation can be performed to remove undesired tissue such as cancer cells. Ablation procedures may also involve the modification of tissue without removal, such as to interfere with or stop electrical propagation through cardiac tissue in a patient with an arrhythmia. Often the ablation is performed by passing energy, such as electrical energy, through one or more electrodes to cause the tissue in contact with the electrodes to heat up to an ablative temperature. Other electrical energies such as laser, microwave, ultrasound, etc., can effect change in tissue. Alternatively, non-electrical therapies such as medications, stem cells, biologics, or cryotherapy can be used to alter the structure and function of tissue.

Atrial fibrillation refers to a type of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria (such as the pulmonary veins) instead of only from the sinus node. This condition overwhelms the atrioventricular node, resulting in an irregular and rapid heartbeat. As a result, blood pools in the atria and increases the risk of blood clot formation.

Atrial fibrillation treatment options are limited. Three known treatments, lifestyle change, medical therapy and electrical cardioversion, all have significant limitations. Electrical cardioversion attempts to restore sinus rhythm but has a high recurrence rate. In addition, if there is a blood clot in the atria, cardioversion may cause the clot to leave the heart and travel to the brain or to some other part of the body, which may lead to a stroke.

Various ablation techniques have been proposed to treat atrial fibrillation, including the Cox-Maze procedure, linear ablation of various regions in the atrium, and circumferential ablation of pulmonary vein ostia. Other linear lesions can target the roof of the left atrium, the mitral valve isthmus, superior vena cava, and the ligament of Marshall.

Certain types of arrhythmias have critical components that require ablation near the normal conduction system of the heart (AV junction and/or His bundle). These arrhythmias typically include paraseptal bypass tracts, AV node reentrant tachycardia, and certain atrial and ventricular tachycardias. Inadvertent ablation misapplications in treating such problems may result in complete heart block and require implantation of a permanent pacemaker, a known possible complication of the procedure. In addition, other untoward events may occur during ablative procedures in which the body may exhibit early signs (such as a change in heart rate, oxygen saturation, and/or blood pressure) which may indicate perforation. When this occurs, the device or catheter creates a hole in the heart wall leading to fluid accumulation in the pericardial sac and a life-threatening condition called cardiac tamponade. Blood needs to be rapidly removed from the pericardial sac by a needle or surgical window along with any supportive measures (blood and/or fluids) as well as possible surgical repair. Each and every untoward event has the potential for medical legal action in which any delay in terminating therapy may be highly scrutinized.

In applying ablation techniques to treat arryhthmias, the distal tip of an ablation catheter is advanced to a desired location in a patient's heart. Radiofrequency or laser energy, for example, is transmitted to the distal tip of a catheter from a point adjacent and/or external to a catherization laboratory upon signal from the doctor or operator to a technician or nurse who operates a generator (such as an RF generator) or a laser, to deliver ablation therapy or energy. Whenever the doctor or operator wants the ablation therapy or energy to be discontinued, the doctor or operator signals the technician or nurse, usually by voice command ("Stop!!!" or "Off!"). However, there is an inherent delay in this procedure, which could result in damage to a patient, such as heart block, perforation, or phrenic nerve paralysis, if the ablation energy is not terminated quickly enough. In addition, it is not very practical for the sterile catheter operator to have direct and immediate control over any switching mechanism contained on the non-sterile generator or console to terminate therapy as they are concurrently configured. Also, these ablation generators and consoles are typically not easily accessible to the operator and, if placed in such a location, would potentially be disruptive to lab staff and operations. Alternatively there could be foot control for the doctor or operator to terminate the ablation energy, but using a foot control may be awkward and difficult to control (especially because two foot pedals would potentially be used in concert: one for fluoroscopy and the other for an on/off switch). In addition, accidentally stepping on the on/off foot pedal switch as it currently functions can potentially turn on therapy and cause inadvertent ablative therapy delivery with unintended injury to the heart, its conduction, and other structures.

Medical devices having on/off or cut-off mechanisms are known. See, for example, U.S. Pat. Nos. 5,951,461, 6,165, 206, 6,235,022, 6,808,499, 7,717,932, and 7,763,033 and U.S. Published Patent Applications Nos. 2007/0233044, 2008/0245371, and 2009/0182325. However, none of these medical devices is an ablation catheter system useful for a cardiac ablation procedure, nor do any of the devices meet the unique demands characteristic of use of an ablation catheter in a catherization laboratory setting. In addition, a method and switching mechanisms have been developed which are compatible with a number of different ablation/therapy systems to prevent inadvertent therapy delivery and provide immediate manual control to the operator.

OBJECTS OF THE INVENTION

It is an object of the invention to provide an improved steerable ablation catheter system.

It is also an object of the invention to provide an improved steerable ablation catheter system where the energy at the distal tip of the ablation catheter can be terminated immediately and abruptly.

It is a further object of the invention to provide an improved steerable ablation catheter system having a kill switch.

It is yet a further object of the invention to provide an improved steerable ablation catheter with a kill switch located in an ergonomic location on the catheter handle.

It is yet a further object of the invention to provide an improved steerable ablation catheter with a kill switch located in an ergonomic location on the handle of the ablation catheter to provide direct and immediate manual access to abruptly terminate delivery of ablation therapy.

It is yet a further object of the invention to provide an improved steerable ablation catheter system with a kill switch located in a cable supplying ablative therapy.

It is yet a further object of the invention to provide a shorter kill switch attached to a male connector at one end and a female connector at the other, to interface with an ablation catheter and a connector cable.

It is yet a further object of the invention to provide a kill switch located on a remote controller or a joy stick with which the operator is manually manipulating a remote navigation or robotic system.

It is yet a further object of the invention to provide a specific and uniquely identifiable voice command system that can activate a kill switch mechanism coupled with an ablation therapy delivery system.

It is yet a further object of the invention to provide an improved steerable ablation catheter system with a foot-operated kill switch.

It is yet a further object of the invention to provide an improved steerable ablation catheter system where the distal portion of the ablation catheter comprises pressure sensors and/or shock absorbing means.

It is yet a further object of the invention to provide a system for providing catheter ablation wherein the system has one or more safety features to minimize the risk of inadvertent damage to heart tissue, such as, for example, perforation or damage to the conduction system or other cardiac structure.

It is yet a further object of the invention to provide an improved system for delivering treatment or therapy to a patient where a kill switch interrupts the treatment or therapy to minimize or avoid damage to a patient.

It is yet a further object of the invention to provide an improved system for delivering treatment or therapy to a patient in a system having an instrument that is in communication with a hand-operated or foot-operated control, where a kill switch interrupts the treatment or therapy to minimize or avoid damage to a patient.

It is yet a further object of the invention to provide a medical system for delivering treatment or therapy to a patient that has a kill switch for interrupting the delivery, where the kill switch can disrupt the delivery directly or can cause an error message to be generated that disrupts the delivery.

It is yet a further object of the invention to provide a medical system for delivering treatment or therapy to a patient that has a kill switch for interrupting the delivery, where the kill switch can disrupt the delivery of therapy by opening the circuit of one or more feedback or sensed ablation system functions such as temperature, impedance, or the like.

It is yet a further object of the invention to provide a medical system for delivering treatment or therapy to a patient that provides the functionality described above via an on/off switch for controlling delivery of therapy.

It is yet a further object of the invention to provide an on/off switch attached to connectors and a cable or just connectors which attach between a medical device and a therapy delivery system.

It is yet a further object of the invention that an entire array of switches or cable-switches is created and customized to the particular type of ablation system, such as cryoablation and/or a particular manufacturer and/or catheter/device type.

It is yet a further object of the invention to provide a connector switch for an ablation system that has a cable and connector as part of the catheter ablation device.

It is yet a further object of the invention to provide a connector cable switch for an ablation system that does not have a cable as part of the catheter ablation device to permit catheter maneuverability.

It is yet a further object of the invention to provide a longer connector cable switch to an ablation system in which phrenic nerve stimulation is occurring to permit the operator to directly sense and feel diaphragm contraction and at the same time to be able to immediately and manually terminate ablation therapy.

It is yet a further object of the invention to provide immediate manual control of a variety of different ablation systems using a connector system interposed between a medical device and it's therapy generator or controller.

It is yet a further object of the invention to provide automatic and computer controlled control of a variety of different ablation systems to detect early signs of inadvertent events and immediately terminate therapy.

It is yet a further object of the invention to provide automatic sensing of phrenic nerve conduction to the diaphragm and immediately cut off therapy when phrenic nerve conduction and/or diaphragm contraction is slightly diminished by a predetermined value.

It is yet a further object of the invention to provide automatic sensing of cardiac conduction such that early evidence of a change in conduction would shut off the system before the development of heart block.

It is yet a further object of the invention to provide automatic sensing of early signs of perforation such that a system would immediately cut off therapy upon detection of those findings.

It is yet a further object of the invention to provide multiple safety features in a catheter ablation system including (1) the ability to immediately and manually terminate therapy by the operator and (2) the ability to monitor and record contact force and pressure of the catheter tip.

It is yet a further object of the invention to provide multiple safety features in a catheter ablation system including (1) the ability to immediately and manually terminate therapy by the operator and (2) the ability to absorb and control the contact pressure and/or force of said catheter as it makes contact with the heart.

These and other objects of the invention will become more apparent from the discussion below.

SUMMARY OF THE INVENTION

The term "kill switch" as used herein refers to a switching mechanism that can immediately and abruptly terminate therapy but cannot initiate therapy by itself. An "on/off" switching mechanism has both the ability to initiate therapy on its own as well as to terminate therapy.

According to the invention, a medical system for delivering ablative treatment or therapy has been provided where the delivery of ablation treatment or therapy can be terminated abruptly and immediately by an operator to prevent heart block and/or other possible procedural complications. In one embodiment of the invention, a kill switch is located on or in the handle of a steerable ablation catheter, preferably in an ergonomic location to provide convenient and easy access by a thumb of the operator. Preferably the kill switch is a button that is depressible and operates to terminate delivery of ablation therapy upon being depressed.

Ablative treatment or therapy can be delivered to a patient for several different purposes. Those purposes include, but are not limited to, cardiac, cardiovascular, urological, and gynecological applications where tissue would be treated.

A typical ablation catheter handle has deflecting levers or controls on the handle for steering the distal portion of the ablation catheter. Preferably the kill switch is located on the handle between the deflecting levers or controls to provide ergonomic thumb access from the catheter handle controlling hand or finger access from the auxiliary hand. This location is advantageous to permit the direct ablation catheter controller the ability to most rapidly terminate the delivery of therapy.

Preferably the kill switch is located in a place or position such that other fingers on the handle, besides the thumb, and the auxiliary hand can stabilize the catheter to a position, while still allowing the additional digit of that hand or the auxiliary hand to depress the kill switch most rapidly and efficiently.

In another embodiment of the invention, the kill switch is positioned on a member integral with the cable that supplies the ablative therapy or energy. For example, the section containing a kill switch can be an integral part of the cable that supplies the ablative therapy and that is connected to the ablation catheter handle. Alternatively, the kill switch can be located in a separate member into which the cable that supplies the ablative therapy and the ablation catheter are connected.

In another embodiment of the invention, the kill switch is positioned between two connectors which would interface at one end with the ablation catheter and the other end would interface with the connector cable and/or with the ablation therapy generator.

In another embodiment of the invention, the kill switch of the ablation catheter system is positioned on a remote controller in which the operator can have immediate and remote access to immediately terminate therapy. The kill switch could be between connectors or between connectors and cables and could be remotely triggered by a remote controller or computer-based system. In addition, the kill switch could be independent and remote and provide signals to the ablation catheter system. Or it could be integrated on a remote controller, handle controller, computer controller, or joy stick to provide remote navigation or manipulation of an ablation catheter or other procedure-related functions.

In another embodiment of the invention, a specific and uniquely identifiable voice command can activate a kill switch mechanism coupled with an ablation therapy delivery system. The switch could be integrated between the catheter and the generator and operate via voice command, or the switch could operate via a voice controller at or near the generator or at computer terminal/remote control device/workstation remotely.

In another embodiment of the invention the kill switch comprises a button that is configured so that when an ablation catheter is "hot" or energized, electricity travels through the catheter handle to light the button or to activate a light, LED, or visual or audible alert in the handle, so that the operator is aware that the catheter is delivering ablation therapy. The button is positioned on the ablation catheter handle so that other features of catheter manipulation via manual means are not disrupted. That is, the operator can easily advance, withdraw, deflect, reverse deflect, and/or rotate the catheter distal portion without interfering with the button function.

A light or audio signal on the ablation catheter handle may provide immediate feedback to the operator to alert him or her that therapy is being delivered. When the button is pressed and the delivery of ablation energy is immediately stopped or killed, the light or audio signal shuts off, an indication that the ablation catheter is no longer ablating.

In another embodiment of the invention, a foot pedal functioning as a kill switch is operatively connected to a source of ablative therapy, a cable supplying ablative therapy, the ablation catheter, a grounding patch or element, or a combination thereof. The foot pedal is positioned to be readily accessible by an operator's foot.

The catheter system according to the invention is designed to enhance the operator's reaction, manually, to prevent or minimize inadvertent delivery of therapy and related complications during catheter ablation. With respect to cardiac catheter ablation, some of these complications include damage to the conduction system (heart block), perforation of the heart tissue itself, and/or damage to adjacent structures such as the phrenic nerve, which powers contraction of the diaphragm and helps with respiration.

In another embodiment of the invention, the kill switch contains a deactivator that deactivates after 24 hours, making said switch non-functional and thereby ensuring that it is disposable.

In normal catherization or electrophysiology lab operations, the ablation therapy may be initiated from a position at some distance from the ablation catheter. This could be at the end of the procedural table or even in another adjacent or distant control room. Such distant locations may include a generator/control console, remote control, remote controller/controller computer terminal, or the like. The kill switch only becomes engaged when the ablation therapy has been activated or enabled; it is not otherwise operable. Preferably there will be an alert mechanism such as a light or LED on or around a kill switch button when the ablation therapy has been energized and is well into the distal tip of the ablation catheter. In one embodiment, depressing the kill switch button can open up the circuit (normal closed, once depressed the circuit is an open kill switch), terminating the ablation therapy, and shutting off the light. The ablation therapy may only be re-initiated when the technician or nurse restarts the radiofrequency generator or laser, at which time the kill switch or alert mechanism, or both, will be reset. Alternatively, a "normal open kill switch" could also function such that therapy could only be delivered if the kill switch is activated by pushing a button and releasing said button would then terminate therapy.

In another embodiment of the invention, the distal end of an ablation catheter comprises pressure sensors and compressible, shock absorbing means, to minimize the chance of perforation or internal damage. The shock absorbing material, such as small springs (or an elastic/flexible ablation contactor), is positioned proximal to the distal electrode. Pressure sensors positioned on or near the proximal surface or edge of the distal electrode measure the forces exerted on the myocardium by the distal section of the ablation catheter.

In another embodiment of the invention, the ablation catheter system will contain at least two safety mechanisms, including an operator-operated manual kill switch and a pressure/force controlling system to optimize the safety to the patient.

In another embodiment of the invention, the ablation system will provide automatic detection capabilities to detect at least one early sign of inadvertent therapy such as phrenic nerve injury, perforation, and/or heart block with the ability to immediately terminate therapy.

There are a variety of kill switches which could be employed in concert with an ablation therapy delivery system. The invention described herein could utilize a myriad of buttons, controls, or switches with indicators that function and/or provide information including LEDs, the flow of electricity notification, audible tones, etc. Many of these have been well described in the electrical engineering literature. The invention also encompasses on/off and kill switches that sense pressure, temperature, or any other parameter.

A normal closed momentary kill switch is one in which the electrical circuit is opened immediately upon depressing the switch itself (typically in the form of a button, although other configurations may exist) and the circuit's impedance would become infinite and ablation therapy delivery would immediately terminate. Once the switch is released, that is, not depressed, the circuit would immediately close and pacing and sensing function from the therapy delivery tip (typically an electrode) would be restored. However, the ability to deliver ablation therapy could not be re-engaged without turning on therapy at the generator source itself. This type of mechanism is ideal for preventing inadvertent delivery of ablation therapy and pacing/sensing function from the therapy electrode or electrodes would only be "momentarily" disrupted during the kill switch deployment and immediately restored upon release of the switch. As above, normal open momentary kill switches could also function in a manner that therapy delivery could only occur with the switch engaged, and therapy termination would occur with release of said switch.

In a preferred embodiment of the invention the kill switch is a mechanical kill switch which is normally in the closed position and, when depressed, transiently stays open. Said kill switch is capable of withstanding 100 watts and 500 kHz with a typical 250 vac and 3 amp rating.

Alternatively, a multi-function switch could control the opening and closing of the kill switch upon each depression or contact. The down side of the latter configuration is the potential for longer disruption of the distal therapy sensing and pacing function. A parallel circuit could separate out therapy delivery disruption from pacing and electrode signal recognition/sensing (i.e., kill switch functionality without disrupting pacing or sensing). In fact, the kill switch can deliver a signal to alter impedance and stop ablation therapy delivery without any effect of sensing or pacing. It can be envisioned that there are numerous ways of providing effective and immediate operator control over therapy delivery via use of a kill switch without having any significant impact (if at all) of electrode functionality (i.e., pacing and electrode signal visibility or sensing). In addition, the kill switch could sense some other function or feedback required for effective therapy delivery and/or function, if this signal is disrupted via the kill switch an error could be detected at the generator and therapy terminated. This is the case with the Medtronic Cardiac CryoAblation System (ARCTIC FRONT®) in which liquid nitrogen is delivered to a balloon/or catheter to freeze tissue. If the electrical connector and some of its functions are disabled (i.e., open circuit) the CryoConsole immediately shuts down. All of these are encompassed in the invention described herein.

In another embodiment of the invention, a kill switch could be positioned on a remote control in order to remotely terminate therapy. This could either be a stand-alone remote control or one that is integrated into a remote control station or remote controller in order to provide control over other aspects of the ablation procedure. It is even possible for this switch mechanism's remote control to be integrated with the controller for remote navigation of an ablation catheter. The kill switch could be located on a handle controller or joy stick or computer controller distal to the catheter manipulator. Alternatively, the kill switch can open the circuit of any signal that is critical to therapy delivery and send an error message to the signal or therapy generator, console, computer (CPU), or the like, in order to terminate the delivery of any type of therapy.

In another embodiment of the invention, the kill switch can create an error signal terminating therapy, for example, by changing impedance, disrupting feedback communications, or the like. Alternatively, a kill switch on a ground cable would interrupt the grounding function and cause an error message to be sent that would disrupt the therapy.

In another embodiment of the invention, an on/off switch can function in each of the above embodiments, in a similar manner and/or configuration as the kill switch configurations above. The "on" component of the switch could be configured to sense human contact prior to being engaged thereby preventing inadvertent therapy by being dropped or leaned against. Other implementations of said on/off switch similar to the kill switch above in a connector-cable or as a connector-switch could provide manual access to the operator in a similar fashion customized to a variety of different ablation systems and manufacturers.

Electricity is necessary to travel from point A to point B to provide ablation therapy (either directly as is the case with radiofrequency energy, or indirectly, as is a controlling or feedback signal monitoring balloon pressure and temperature in a cryoablation balloon). If a switching mechanism such as a kill switch were interposed between the electrical circuit of point A to point B, it could be configured such that the circuit is normally closed and momentarily manually depressing the switch would open up the circuit and thereby prevent electricity from proceeding, thereby terminating therapy (normally closed momentary kill switch). Alternatively, the kill switch could be configured to be normally open and depressing said switch would be necessary prior to delivery of ablative therapy initiated by traditional means (normally open momentary kill switch). Releasing the depressed kill switch in this latter configuration would terminate therapy.

In both examples, the kill switch, unlike an on/off switch is incapable of turning on therapy itself. Therefore, the unique application of the kill switch to catheter ablation is its ability to prevent inadvertent therapy delivery. You cannot step or accidentally press a kill switch and turn on ablation therapy. The kill switch described herein is a mechanical momentary kill switch. The momentary kill switch may be preferable for the application of terminating ablation therapy, but it is not absolutely necessary. The kill switch can be depressible and lock into position. A tested catheter handle version contained such a switch that, once depressed, held the closed position, and when depressed again, opened the circuit to terminate therapy. Each depression mechanically reset the circuit accordingly.

Other types of configurations could include an automatically triggered kill switch based on a sensed algorithm for early detection of adverse events such as phrenic nerve injury. The phrenic nerve could be stimulated and phrenic nerve conduction and/or diaphragm contraction could be recorded. A predetermined minimal change in threshold could trigger the kill switch to automatically terminate therapy in this instance. Similarly, early signs of perforation and/or changes in conduction could trigger the kill switch to terminate therapy thereby reducing the chance of a significant complication. In addition, the kill switch or an on/off switch could function via a remote controller (using a transmitter/receiver configuration such as a television remote control using infrared or radio wave signals). Alternatively, these switches could also function via voice or sound command and can have some preprogrammed actuators, signals, and voice programs.

Regardless of whether the switching mechanism is an on/off switch of kill switch many variations are possible, including a depressible button, toggle switch, temperature or infrared sensor, or switch button, for example. For standard radiofrequency a switching mechanism would typically need to be rated for at least 100 Watts at 500 kHz with a 250 vac/3 amp rating. Error signals and other types of sense signals may have different and perhaps less energy requirements to function appropriately. In addition, standard radiofrequency ablation typically delivers therapy from the distal ablation electrode to a grounding patch. A single pull kill switch may operate effectively interposed between the conductor or wire that goes to that electrode. However, more complicated and future ablation systems may deliver energy through more than one electrode and a multiple pull kill switch would be necessary to disrupt all therapy immediately. The same goes for critical error signals necessary for feedback and surveillance of non-radiofrequency energy (e.g., cryoablation). These signals may require more than one pull (or one open conductor) to shut down therapy. In addition, it is conceivable that the switching mechanism itself can produce its own error signal and disrupt the controller/generator and terminate therapy as well. A number of different switching mechanisms and configurations can achieve the goal of this novel therapy intended as a more efficient means of rapidly terminating therapy and avoiding unnecessary complications.

In another embodiment of the invention, in an improved ablation catheter system comprising a longitudinally extending catheter having a proximal end and a distal end, a handle attached to the proximal end of the catheter, a mechanism at the distal end of the catheter for delivering ablation therapy to a desired location, such as tissue, and a generator or controller of ablation therapy in communication with the handle, the handle and the distal end of the catheter, or the handle, the catheter, and the distal end of the catheter, the ablation catheter system comprises a switching mechanism which is capable of causing abrupt termination of delivery of ablation therapy by manual, automatic, remote, or voice-operated operation.

In another embodiment of the invention, the switching mechanism is positioned between the ablation catheter distal tip and the generator or controller of ablation therapy, including on or in the therapy-producing generator or controller.

In another embodiment of an ablation catheter system of the invention, the kill switch is interposed on or in communication with one or more conductor wires contained within the ablation catheter, an electrical connector cable, a separate device connected between the catheter and a therapy-producing generator or controller, or the therapy-producing generator or controller.

In another embodiment of an ablation catheter system of the invention, the switching mechanism is an on/off or kill switch which is contained on and/or within the handle, which is in or in communication with a connector cable, a separate device connected between the catheter and the therapy-producing generator or controller, or the therapy-producing generator or controller.

In another embodiment of an ablation catheter system of the invention, the switching mechanism comprises wires, connectors, a switch, and a protective enclosure to permit operation on a sterile medical field.

In another embodiment of an ablation catheter system of the invention, the switching mechanism is interposed on or in communication with at least one conductor wire contained within the catheter and a cable which leads from the catheter to a therapy-producing generator or controller and which operation of the switching mechanism permits therapy, terminates therapy, or permits and terminates therapy.

In another embodiment of an ablation catheter system of the invention, the switching mechanism comprises a depressible button, a touch sensitive switch, a toggle switch, a pressure- or temperature-sensitive sensor, or the like.

In another embodiment of an ablation catheter system of the invention, the switching mechanism is positioned between steerable levers on the handle and/or catheter body to provide ergonomic thumb, finger, or thumb and finger access.

In another embodiment of an ablation catheter system of the invention, wherein the determination of whether a switching mechanism is to be positioned on the handle of the catheter, in a cable having a distal end that is inserted into the handle or rigid portion of a handle of a catheter, in a short cable segment to be attached to the proximal end of a cable extending from the handle of a catheter and the proximal end of a cable from a therapy generator or controller, or in a long cable segment to be attached to the proximal end of a cable extending from the handle of a catheter and the proximal end of a cable from a therapy generator or controller, is based upon factors such as the design and configuration of the catheter, the ablation therapy, and the location of the site to be ablated.

In another embodiment of an ablation catheter system of the inventions, wherein the location of the switching mechanism as well as its mode of incorporation into the catheter ablation system is determined by accessibility to a manufacturer's platform, the type of catheter and its design and presence or absence of a built in cable at the end, the type of procedure, position of the patient's catheter access site, the operator's position, and the operator's necessity to immediately monitor for adverse effects of the therapy on the patient.

In another embodiment of an ablation catheter system of the invention, the design, configuration, and position of said switching mechanism and its application is determined by the type of procedure, type of catheter and its design, catheter access point, position of the patient, position of the operator, maneuverability of the medical device (i.e., catheter), as well as the operators ability to monitor for inadvertent therapy while performing said procedure. Such a design may consider a longer cable with the switch mechanism positioned more proximal to the operator such that the operator could perform a cryoablation procedure from the groin and have access to the switch in order to manually feel the contraction of the diaphragm during phrenic nerve stimulation and at the same time have manual control of the therapy with the ability to immediately shut off therapy if diaphragm contraction (or its surrogate) diminishes in order to avoid permanent phrenic nerve damage. A shorter connector switch could attach directly to a Boston Scientific BLAZER® radiofrequency ablation catheter since that device already has approximately 8 inches of cable at the end of said catheter permitting manual manipulation. Other radiofrequency ablation catheters such as the Medtronic RF ablation catheter, the Johnson & Johnson Biosense Webster THERMOCOOL® ablation catheter, and the St. Jude Medical SAFIRE TX™ ablation catheter have handles which terminate with just a connector. Each of these handles has an integral plug for receiving a connector from a cable or device. A switching mechanism device which includes enough of a cable would help such that those catheters could be easily rotated without making manipulation awkward.

In another embodiment of an ablation catheter system of the invention, the switching mechanism is positioned in a long cable segment to be attached to the proximal end of a cable extending from the handle of a catheter and the proximal end of a cable from a therapy generator or controller for cryoablation, so that an operator can operate the switching mechanism and feel a patient's diaphragm contractions to prevent phrenic nerve paralysis.

The variety of connectors and cables useful with ablation catheters according to the invention means that one carrying out the invention herein will have to select the appropriate cable, device, and/or connector to match up to the handle of the ablation catheter used. The ablation catheter described above which terminate without any built-in cable may require a cable plus switching mechanism to permit catheter maneuverability. The Boston Scientific ablation catheter which has approximately 8 inches of cable built in at the end can utilize a connector switch with or without a cable. A longer cable may be required for a cryoablation procedure performed from the groin, if the operator is to feel diaphragm contraction force while at the same time feeling a switch attached to a catheter. A remote control could trigger the switch mechanism itself. Such a control could have a transmitter/receiver configuration and operate the switching mechanism in a catheter, connector, cable, generator, computer controller or combination thereof.

In another embodiment of an ablation catheter system of the invention, the switching mechanism is located so that other fingers on the handle and the auxiliary hand can stabilize catheter positioning while still allowing an additional digit of that hand or the auxiliary hand to depress the switching mechanism most rapidly and effectively.

In another embodiment of an ablation catheter system of the invention, the location of the switching mechanism as well as its mode of incorporation into the catheter ablation system are determined by accessibility to a manufacturer's platform, the type of catheter and its design and presence or absence of a built in cable at the end, the type of procedure, position of the patient's catheter access site, the operator's position, and the operator's necessity to immediately monitor for adverse effects of the therapy on the patient.

In another embodiment of an ablation catheter system of the invention, the switching mechanism is positioned in a long cable segment during cryoablation, so that an operator can manually operate the switching mechanism and feel a patient's diaphragm contraction at the same time to prevent phrenic nerve paralysis.

In another embodiment of an ablation catheter system of the invention, the switching mechanism is in the most appropriate place to allow an operator to both manually perform an ablation procedure and to manually terminate therapy.

In another embodiment of an ablation catheter system of the invention, the switching mechanism is positioned between two connectors and wires in either a cable plus enclosure or just an enclosure, all intended to transmit and/or control ablation therapy.

In another embodiment of an ablation catheter system of the invention, the switching mechanism can be engaged only after ablation therapy has been initiated from the therapy-producing generator and/or computer controller.

In another embodiment of an ablation catheter system of the invention, the switching mechanism has an alert function.

In another embodiment of an ablation catheter system of the invention, the switching mechanism can receive a signal from a remote controller to terminate therapy.

In another embodiment of an ablation catheter system of the invention, the switching mechanism is voice-, touch-, or sound-activated and is coupled either directly or remotely to the ablation therapy delivery system.

In another embodiment of an ablation catheter system of the invention, a receiver has been programmed to recognize an operator's voice, a certain command or commands, or a combination thereof.

In another embodiment of an ablation catheter system of the invention, the switching mechanism is controlled remotely, wired or wirelessly, to permit immediate and remote therapy termination.

In another embodiment of an ablation catheter system of the invention, the switching mechanism is a kill switch that either (1) is normally a closed circuit and when the switch is engaged it opens the circuit, forcing the ablation catheter system to shut off its therapy, and then closes immediately, thereby restoring full functionality of the system without re-initiation of therapy delivery or (2) is normally an open circuit which requires the switch to be engaged such that the circuit is closed thereby permitting the transmission of ablation therapy, whereas disengaging said switch immediately terminates therapy.

In another embodiment of an ablation catheter system of the invention, the kill switch can operate as a fixed switch such that engaging the switch performs one function such as closing an electrical circuit in order to permit ablation therapy delivery and re-engaging said switch opens an electrical circuit thereby terminating therapy; or a momentary mode such that an electrical circuit is either open or closed as long as the switch is manually engaged.

In another embodiment of an ablation catheter system of the invention, the switching mechanism works directly through the therapy generator or controller.

In another embodiment of an ablation catheter system of the invention, the switching mechanism is a kill switch that momentarily opens, forcing the ablation catheter system to shut off its therapy, and then closes immediately, thereby restoring full functionality of the system without re-initiation of therapy delivery.

In another embodiment of an ablation catheter system of the invention, the switching mechanism or kill switch comprises parallel circuitry in which ablation therapy delivery can be immediately disrupted without interrupting any of the system's electrical capabilities.

In another embodiment of an ablation catheter system of the invention, the switch mechanism is depressible and resettable.

In another embodiment of an ablation catheter system of the invention, in an improved ablation catheter system comprising a longitudinally extending catheter having a proximal end and a distal ends, a handle attached to the proximal end of the catheter, a mechanism at the distal end of the catheter for delivering ablation therapy, and a source of ablation therapy in communication with the handle, the catheter, and the distal end of the catheter, the improvement wherein the system has a switching mechanism and one or more additional safety features to minimize the risk of inadvertent damage to tissue, especially heart tissue.

In another embodiment of an ablation catheter system of the invention, shock absorbing materials are interposed between the distal tip of the catheter and the catheter to help absorb the contact force and minimize pressure delivered to tissue and the risk of inadvertent damage. Alternatively, the tip may be made of an elastic and or flexible material in order to help absorb and cushion the contact.

In another embodiment of an ablation catheter system of the invention, one or more contact sensors are interposed between the ablation therapy delivery tip and the absorbent material to measure the degree of contact.

In another embodiment of an ablation catheter system of the invention, one or more contact sensors measure pressure, force, or both pressure and force and the operator has direct manual access to terminate therapy.

In another embodiment of an ablation catheter system of the invention, haptics are coupled to the handle to provide feedback to an operator as to the amount of contact pressure that is being delivered to the tip of the ablation delivery system within the human body.

In another embodiment of the invention, a system for preventing inadvertent damage to heart tissue comprises an immediately accessible kill switch and features to detect and minimize excessive force delivered to the tip of an ablation catheter system within the heart.

In another embodiment of an ablation system of the invention, a system for preventing inadvertent damage to the heart and/or circulatory system and/or pericardial space during delivery of ablative treatment or therapy comprises a plurality of safety features, including (1) an immediately accessible on/off or kill switch and (2) one or more force or pressure sensors to detect and minimize excessive force delivered to the tip of an ablation catheter system.

In another embodiment of an ablation system of the invention, the system is an operator-controlled system which permits the operator to have immediate manual control over (1) the amount of force applied to the end or ends of an ablation system and (2) permitting ablation therapy, terminating ablation therapy, or permitting and terminating ablation therapy.

In another embodiment of the invention, a medical device which fastens over a first connector and a connectable second connector of a connection cable linked to a medical device for delivering medical treatment or therapy, contains a mechanism for easily separating the first and second connectors and thereby interrupting treatment or therapy.

In another embodiment of a medical device of the invention, the medical device also permits easy reconnection of the connectors.

In another embodiment of the invention, a rapid cable connect/disconnect device for immediate separation of a male cable connector and a female cable connector, comprises a component which grasps both connectors, maintains alignment of the connectors to one another, unlocks any locking mechanism, and separates said connectors, and is also capable of mechanically reconnecting or re-coupling the cable connectors in an aligned manner to restore continuity.

In another embodiment of the invention, a device can be used in concert with an ablation catheter system such that rapid cable disconnection results in termination of ablation therapy to minimize damage from inadvertent therapy delivery and rapid cable reconnection can restore full functionality of the ablation catheter system.

In another embodiment of the invention, a switching mechanism for use with an ablation catheter system comprises:

a first wired or wireless component for direct manual activation, which is capable of being attached to or placed adjacent to an ablation catheter handle, and a second wired or wireless component coupled to the first component to receive, transmit, or receive and transmit a switching signal generated by the first component, to provide direct manual control of the delivery of ablation therapy.

In another embodiment of the invention, the first component can be attached to the catheter handle with a stretchable sleeve, a clip, a connector, or sterile adhesive.

In another embodiment of the invention, a rapid cable connect/disconnect device having a kill switch provides for immediate connection or separation of a male cable connector and a female cable connector. The rapid cable connect/disconnect device comprises a component with male and female receptors which grasp the respective female and male ends of the connectors, maintains alignment of the connectors to one another, and optionally unlocks any locking mechanism. The female receptor of the rapid cable connect/disconnect device engages the male connector and the male receptor of the rapid cable connect/disconnect device engages the female connector, so as to separate the connectors, and the rapid cable connect/disconnect device is also capable of mechanically reconnecting or re-coupling the cable connectors in an aligned manner to restore continuity.

In another embodiment of the invention, a rapid cable connect/disconnect device with a kill switch can be used in concert with an ablation catheter system such that rapid cable disconnection results in termination of ablation therapy to minimize damage from inadvertent therapy delivery and rapid cable reconnection can restore full functionality of the system.

In another embodiment of the invention, a device for immediate separation of first and second cable connectors comprises a first tubular or substantially tubular member that is capable of encircling and grasping the first cable connector, a second tubular or substantially tubular member that is capable of encircling and grasping the second cable connector, and a bridge member connecting the first and second tubular or substantially tubular members, wherein, when a portion of the bridge member is pushed downward, a latch disengages and the tubular or substantially tubular members move away from each other and cause the cable connectors to disengage or disconnect.

In another embodiment of the invention, the device facilitates easy reconnection of the first and second cable connectors.

In another embodiment of the invention, an on/off switch or kill switch is positioned between two connectors in a component. The component can be positioned relative to an ablation catheter handle based on one or two cable connectors of varying lengths. The component may be attached to two variable length cable connectors, one of which is attached directly to the ablation catheter handle, or, dependent upon which model ablation catheter is used, the component may be attached directly to the proximal end of the handle of the ablation catheter. The lengths of the cable connectors may vary depending upon where the operator wants the component (with the on/off or kill switch) to be positioned relative to the ablation catheter handle. If there is a cable connector between the ablation catheter handle and the switching component, that switching component would preferably be disposable, and the cable connectors could each be reusable/resterilizable. However, it is possible that the switching component and cables could be either disposable or reusable/resterilizable.

In another embodiment of the invention, a component comprising a kill switch is configured for dual use, that is, to be convertible from manual to foot operation. More particularly, the component would be configured so that it could be functionally connected to an ablation catheter and be positioned within the sterile field for manual operation by the operator to kill ablation function and so that it could alternatively be positioned for foot operation. For example, the component could operate on a sterile field in a first mode of operation as a manual kill switch (with a kill switch on the top surface of the component for manual operation), and the component could operate and be positioned in a second mode such that the switch component could be opened up and placed on the floor (non-sterile) such that the foot could control a pedal inside the component in order to trigger the kill switch and terminate therapy.

In another embodiment of the invention, an on/off switch or kill switch can be attached directly onto an ablation catheter handle via suitable means, such as a sterile adhesive, a clip, or a sleeve (that would slide over the front or back of the catheter handle). If the switch is connected to the ablation therapy system via a connector cable—either contained therein or as a separate device interposed between connector cables—the switch could double back toward the catheter handle and clip on, slide on, or adhere to the handle by a number of means to the catheter handle such that the switch itself functions on the handle.

In another embodiment of the invention, a connector cable could be configured such that all of the wires are contained within the connector cable and the wire or wires necessary for switching off therapy separately branch off to connect to an on/off or kill switching mechanism. That switching mechanism can be attached to an ablation catheter handle in a number of different ways, such as by adhesive, a sleeve, or a clip. The input and output wires of the switching mechanism could be contained within a thinner sleeve that could reach the ablation catheter handle and adhere to the ablation catheter handle to permit catheter manipulation and have the switching mechanism on the ablation catheter handle itself. The connector cable will consist of a thicker and stiffer cable at its proximal end which connects to a generator or control console and a distal member containing a thinner, more flexible wiring to the switching mechanism which can be placed on the ablation catheter handle. The separate switching mechanism could essentially be a thin wire that can extend from the end of the connector cable proximal to the catheter and easily attach to the ablation catheter handle without tangling during manipulation and permit easy access to the switch on the ablation catheter handle to terminate therapy manually.

In another embodiment of the invention, a connector cable looks like a regular cable and has a separate terminus for a thinner switching mechanism which could attach to the connector cable. This mechanism if not engaged would allow the connector cable to operate like a regular connector cable, but if the switching mechanism is attached, it then has the ability to terminate therapy. The switching mechanism can operate off the handle or it can attach directly to the ablation catheter handle.

In another embodiment of the invention, a switching mechanism attaches directly onto an ablation catheter handle. The switching mechanism can look similar to FIG. 1A such that it can be placed in an easily accessible position on the ablation catheter handle to provide easy ergonomic access to the switching mechanism to easily terminate therapy. The switching mechanism itself can be wireless (i.e., no direct wires terminate from the switch directly into the ablation catheter or its connector cable). However, the switching mechanism can adhere to the ablation catheter by a number of ways, such as adhesive, a clip, or a flexible stretchable sleeve, and can terminate therapy by transmitting a signal to the receiver switching mechanism incorporated in a connector cable, separate device, generator, console, or computer controller. Alternatively, the switching mechanism can create a signal which could interrupt therapy by creating an error signal. For example, a stretchable sleeve slid over the proximal end of the handle may contain many turns of an electrical coil. When the sleeve is depressed (engaged), it could send a current throughout the coils to create an electrical current through the ablation wires contained in the handle via inductance, changing the signal enough that an error could be detected by the generator or controller console and terminate therapy. Other types of error and/or jamming signals could also terminate therapy. In essence the method provides a free standing, sterile method to achieve an on/off switch or kill switch functionality with a wireless mechanism which can adhere or attach to the ablation catheter handle.

In another embodiment of the invention, a sealed reusable connector cable could contain a kill switch which looks and feels like a more standard cable (though it may have a bulge for the separate kill switch mechanism). This switch/cable could be reusable and resterilized (as well as disposable). This switching mechanism contained within the cable has a receiver function. A separate sterile disposable switch which could clip to the handle, slide over the front or back as an elastic or stretchable sleeve, or attach to the handle by some other adherent mechanism and could serve as a transmitter switch which when activated (i.e., depressed for example) it would send a signal to the transmitter and terminate therapy. In addition, the kill switch receiver could be contained within the ablation generator, console, or computer controller.

In another embodiment of the invention, an on/off or kill switch mechanism could be built-in to a device which attaches to or rides over the proximal end of an ablation catheter handle which terminates with only a connector and no cable. Examples of such catheters include Medtronic's RF catheter, St. Jude Medical's SAFIRE catheter, and Biosense Webster's THERMOCOOL catheter. The device could comprise a separate component that (1) has an integral switching mechanism, (2) plugs into the proximal end of the ablation catheter handle, and (2) has a male or female receptacle for receiving a connector from a cable. Alternatively, the device could comprise the distal end of a cable that (1) has an integral switching mechanism to attach to the ablation catheter handle and (2) plugs into the proximal end of the ablation catheter handle. In essence, this device can permit the switching mechanism to appear as if it is part of the ablation catheter handle itself.

BRIEF DESCRIPTION OF THE DRAWINGS

FIG. 2 is a schematic representation of an embodiment of the invention where a kill switch is positioned in a member that can be positioned between a cable supplying ablative energy and an ablation catheter;

FIG. 3 is a schematic representation of an embodiment of the invention where a kill switch is positioned in a cable supplying ablative energy;

FIG. 4. is a schematic representation of a foot pedal that can act as a kill switch;

FIGS. 5 and 6 are schematic representations of the distal end of an ablation catheter according to the invention;

DETAILED DESCRIPTION OF THE INVENTION

Figure 1A:
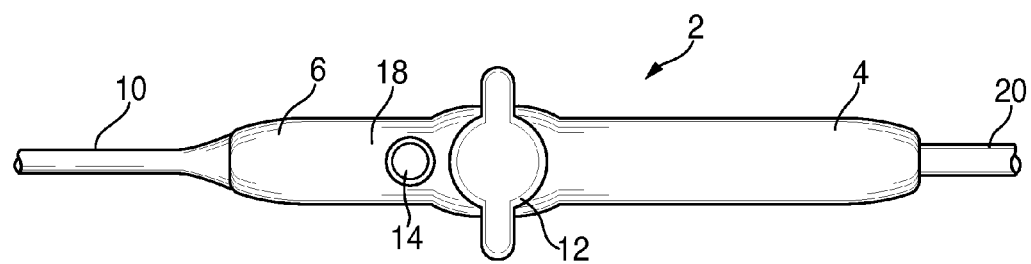
FIG. 1A is an oblique view of the handle of an ablation catheter, which handle represents an embodiment of the invention.
Figure 1B:
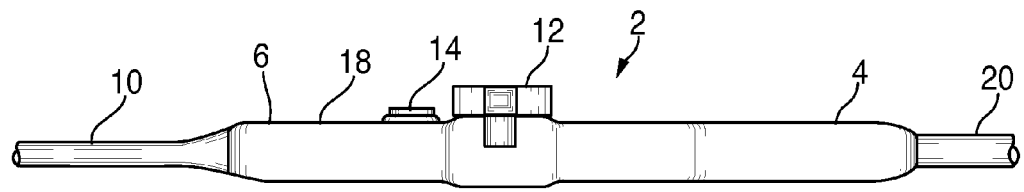
FIG. 1B is a lateral view of the handle shown in FIG. 1A.

The invention can perhaps be more appreciated from the embodiments of the invention set forth in the drawings. In FIGS. 1A and 1B, a steerable ablation catheter handle 2 has a proximal portion 4 and a distal portion 6. Distal portion 6 engages a distally extending ablation catheter 10, and a pivoting lever mechanism 12 steers ablation catheter 10. A red depressible button 14 is positioned on the upper surface 18 of handle 2. When ablation energy enters handle 2 from proximal cord or cable 20, button 14 lights up.

In the embodiment of the invention set forth in FIG. 2, a connector 30 attached to a cable 32 from an ablation therapy supply (not shown) can be connected to a first, male connector 38 of a member 40 having a momentary mechanical or digital kill switch 42 with a button 43. A second, female connector 44 of member 40 can be connected to connector 46 attached to a cable 50 of an ablation catheter (not shown) or to a catheter such as the Biosense Webster THERMOCOOL catheter that comprises a receptacle for connector 44 at its proximal end (not shown).

With regard to kill switch 42, when kill switch 42 is in a rest or closed position, that is, button 43 extends away from the surface, the circuit between cable 32 and cable 50 is closed. Pushing button 43 causes switch 42 to open the circuit between cable 32 and cable 50, disrupting therapy. Switch 42 can be rated at, for example, 250 vac and 3 amp. The lengths of cables 32 and 50 can be varied dependent upon factors such as the desired placement of member 40, the catheter used, or the positions of other equipment.

Member 40 may comprise a clam shell outer casing that is sealed and water resistant. Alternatively, the casing could be injection molded. Preferably member 40 has insulated copper wire 48 (dotted lines) connecting connector 38, switch 42, and connector 44. Connector 44 may be, for example, a Redell 10-pin connector, which would be compatible with the Boston Scientific BLAZER catheter. Other pin connectors may be chosen to be compatible with other catheters available from, for example, Biosense Webster (Johnson & Johnson), Medtronic, and St. Jude Medical.

FIG. 3 represents an alternative embodiment where a cable 52 from an ablation therapy source (not shown) comprises a section 54 with a kill switch 56. A connector 60 attached to cable 52 is capable of connecting to a connector 62 of a cable 64 attached to an ablation catheter (not shown). Catheters such as St. Jude Medical catheters, Medtronic RF ablation catheters, and Biosense Webster catheters that do not have any cable extending as part of the ablation catheter may benefit from a connector-cable-kill switch-cable-connector configuration rather than a straight connector-kill switch-connector configuration to provide more catheter maneuverability rather than a longer stiffer handle. The customer could choose and select the particular length of cable, location, and/or configuration that best meets their needs. The Medtronic Cardiac CryoAblation catheter (ARCTIC FRONT) to freeze pulmonary veins on the right side could be connected to a longer cable-kill switch-cable system such that the operator could reach and feel diaphragm contraction during phrenic nerve stimulation while at the same time having the other hand on the kill switch to immediately detect any adverse effects to the phrenic nerve and immediately terminate therapy.

In the embodiment of the invention shown in FIG. 4, a foot pedal 70 is operatively connected through a cable 72 connected at connector 76 to an ablation therapy source 78. Stepping on foot pedal 70 would cause therapy source 78 to immediately cease delivery of therapy.

FIGS. 5 and 6 each are a schematic representation of the distal section of an ablation catheter. In FIG. 5, a distal electrode 80 is positioned distal to standard electrodes 82. Pressure sensors 86 are positioned on the proximal surface 88 of distal electrode 80, and a single shock absorber 90 is positioned proximal to distal electrode 80. In FIG. 6, a distal electrode 92 is positioned distal to standard electrodes 94. Pressure sensors 96 are positioned on the proximal surface 98 of distal electrode 92, and several shock absorbers 100 are positioned proximal to distal electrode 92. It is conceivable that two or more safety features could be incorporated into the same catheter such that the operator would have the immediate ability to terminate therapy manually as well as safely control the force and/or pressure delivered to the heart. In the event that pressure sensed exceeds a predetermined level or value, an operator would see that that level or value had been exceeded and trip a kill switch. Alternatively, a controller senses that a predetermined level or value has been exceeded and automatically generates an error message or signal that will cause therapy to cease.

Figure 7:
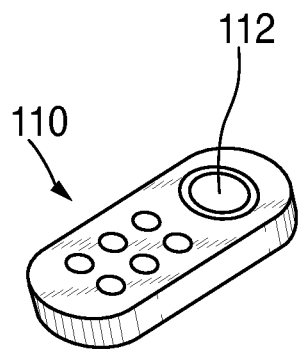
FIG. 7 is a schematic of the kill switch on a remote handle controller which can remotely manipulate an ablation catheter and/or system.

In FIG. 7 a manual remote 110 comprises a kill switch 112. Remote 110 is electrically connected either wired or wirelessly with a receiver (not shown) that is functionally connected to an ablation therapy delivery system. Activation of kill switch 112 results in interruption of therapy delivery by the ablation therapy delivery system. In another embodiment, the kill switch could be connected between the catheter and the therapy delivering generator and/or console and triggered via a remote control device.

Figure 8:
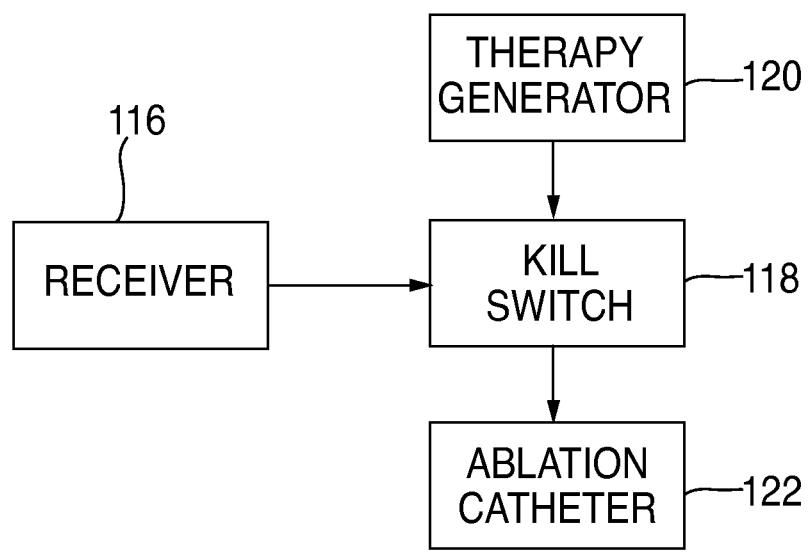
FIG. 8 shows a schematic diagram of voice command activated kill switch mechanism for remotely activating the kill switch with a precise and learned verbal command.

FIG. 8 is a schematic diagram of a voice activated kill switch for an ablation therapy delivery system. A receiver 116 receives a voice command from an operator, where the receiver preferably has been programmed to recognize the operator's voice, a certain command or commands, or a combination thereof. Receiver 116 is functionally connected to a kill switch 118, which is interposed between a therapy generator 120 and an ablation catheter 122. Optionally kill switch 118 can be functionally connected directly to either therapy generator 120 or ablation catheter 122.

It is conceivable that said configuration for the kill switch could also be an on/off switch instead contained directly within the catheter handle or adapted to a variety of connectors and cables to provide manufacturer/catheter and operator optimized functionality.

Figure 9:
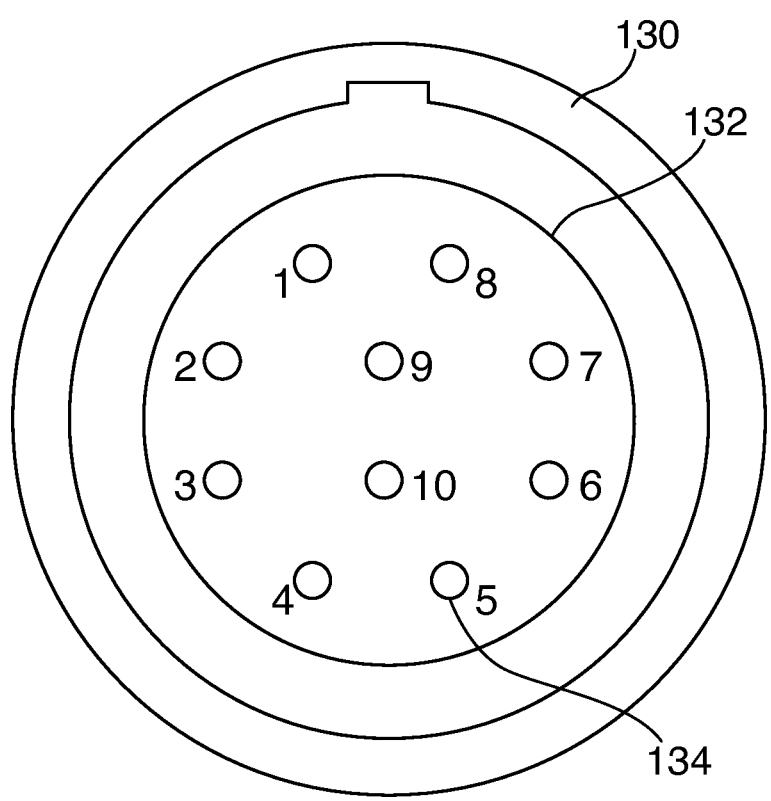
FIG. 9 is a view of an end of a plug for a radiofrequency cable useful according to the invention.

FIG. 9 is a view of the end of a cable plug or connector 130 where a rigid or semi-rigid cylindrical surface 132 surrounds pins 134. Pins 134 are further identified as "1" to "10" and have the functions set forth as follows:

| PIN NO. | FUNCTION |
| --- | --- |
| 1 | Ablation electrode #1 |
| 2 | Not used |
| 3 | Thermocouple (constantan) |
| 4 | Thermocouple (copper) |

| PIN NO. | FUNCTION |
| --- | --- |
| 5 | Band electrode #2 |
| 6 | Band electrode #3 |
| 7 | Band electrode #4 |
| 8 | Connection check |
| 9 | Connection check |
| 10 | Not used |

It is within the scope of the invention that a switching mechanism will not interrupt all the cable functions but only selected ones, so that other functions can continue. Here, for example, interrupting the signals associated with pin 1 would terminate the ablation function.

Figure 10A:
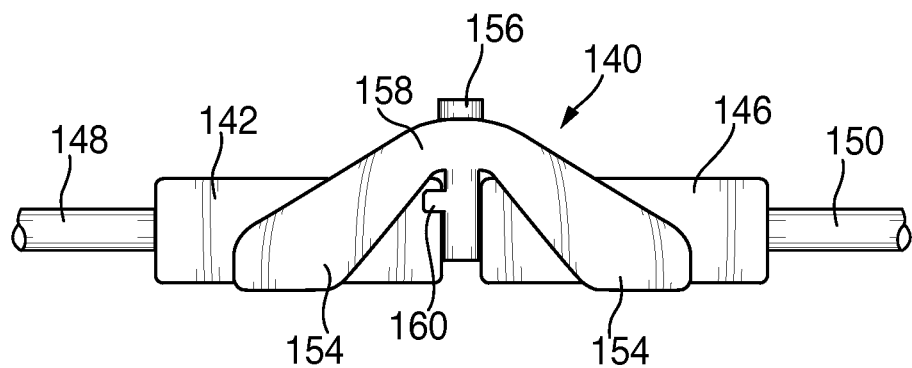
FIGS. 10A and 10B are schematic drawings of a simple mechanical disconnector according to the invention.
Figure 10B:
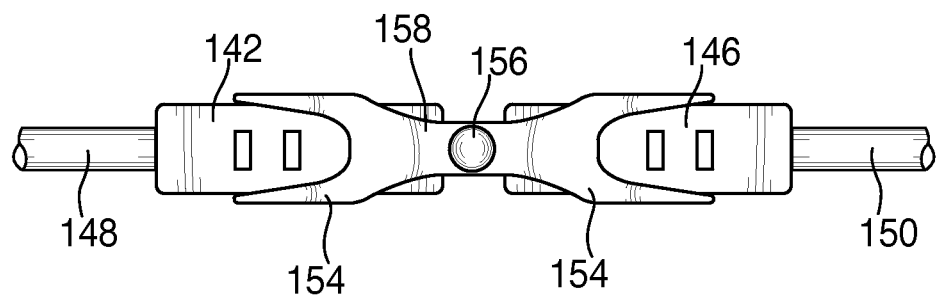

FIGS. 10A and 10B are top and lateral schematic representations of an ablation therapy safety device where a safety member 140 is positioned adjacent female end 142 and male 146 end of a cable 148 and a cable 150, respectively. Safety member 140 comprises sleeve or support members 154 that engage respective ends 142, 146. A pressure point or button 156 is positioned on a bridge member 158 connected to support members 154. When button 156 is pushed in a downward direction, that is, toward bridge member 154, a latch 160 on female end 142 is engaged/unlocked and support members 154 push against cable ends 142 and 146 to cause them to separate a predetermined distance, thus interrupting the flow of therapy through cables 148 and 150. When ends 142 and 146 are pushed back together, ablation therapy can flow through cables 148 and 150 once the ablation therapy generator or source (not shown) is re-started.

Figure 11:
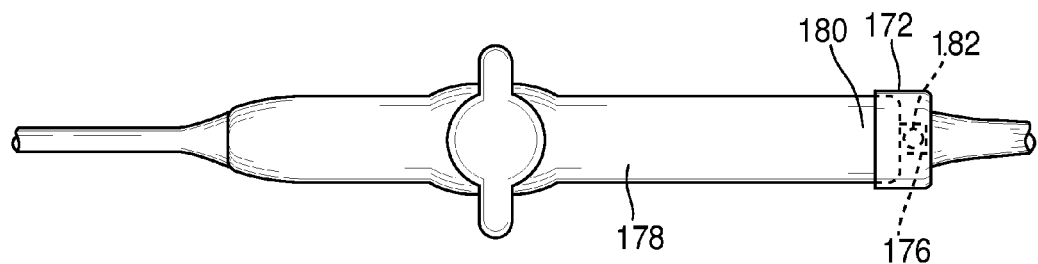
FIG. 11 is a schematic drawing of a variation of the manner in which a kill switch can be positioned on and in communication with a catheter handle and a cable.

FIG. 11 represents a top view of a cable 170 with a molded cable connector 172 that is received in and engages a receptacle 176 in catheter handle 178. Cable connector 172 engages or extends slightly over the proximal end 180 of catheter handle 178, to provide support for, for example, a kill switch button 182 that is functionally connected to cable connector 172 and/or cable 170.

Figure 12A:
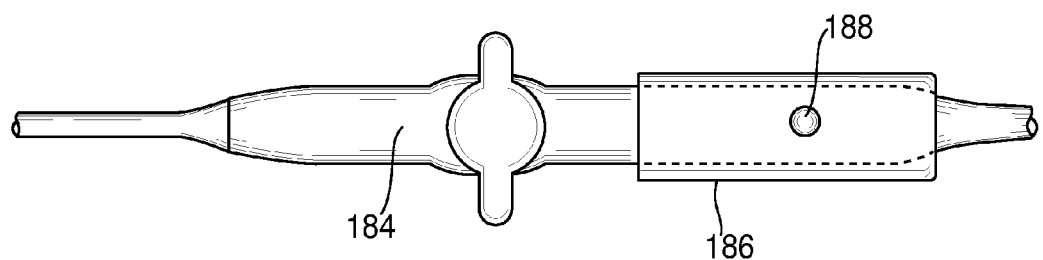
FIGS. 12A and 12B are schematic drawings of flexible sleeves that can be positioned over catheter handles.
Figure 12B:
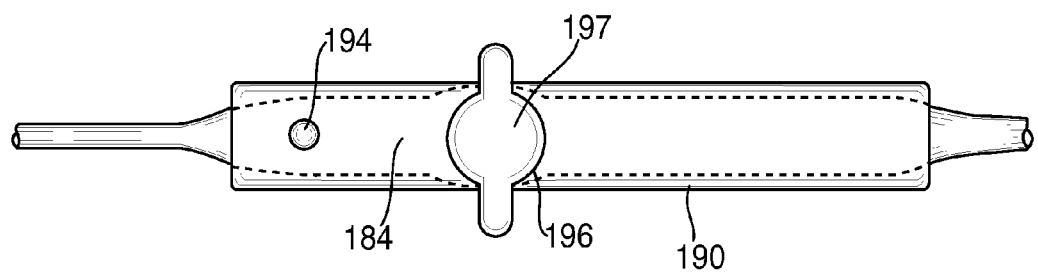

FIGS. 12A and 12B are schematic representations of a catheter handle 184 having a flexible gripper sleeve surrounding the outer surface of catheter handle 184. In FIG. 12A, a gripper sleeve 186 having a length approximately one-half of the length of catheter handle 184 has been slipped over and is in position on catheter handle 184. Sleeve 186 has a on/off or kill switch 188 that is in wired or wireless communication with catheter handle 184, cable 189, or some other component that can affect or interrupt the delivery of ablation therapy. The gripper sleeve 190 shown in FIG. 12B has a length substantially the length of catheter handle 184 and has been slipped over and is in position on catheter handle 184. There is an opening 196 that fits around deflector 197. Sleeve 190 has a on/off or kill switch 194 that is in wired or wireless communication with catheter handle 184, cable 189, or some other component that can affect or interrupt the delivery of ablation therapy.

Sleeves 186 and 190 can comprise any medically acceptable woven or non-woven flexible material, such as any flexible and sterilizable polymeric member that can fit over and on a catheter handle. Advantageously the sleeve material will provide comfort and an enhanced gripping surface, that is, grippability, for the operator's hand or fingers.

Figure 13:
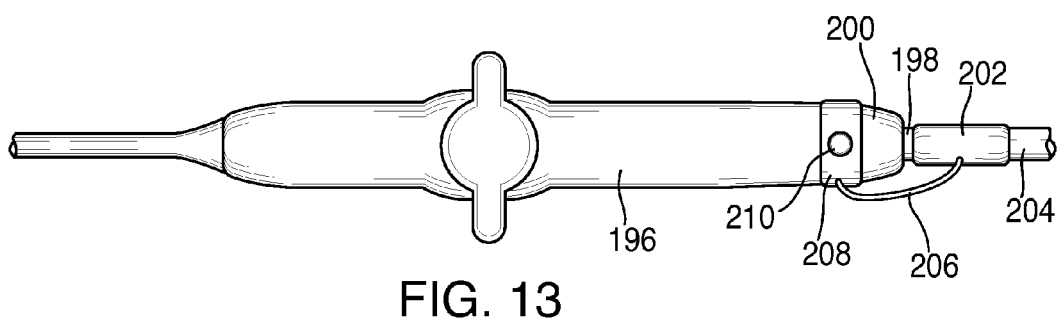
FIG. 13 is a schematic drawing of another embodiment of the invention where a kill switch can be positioned on and in communication with a catheter handle and a cable.

FIG. 13 represents a top view of a catheter handle 196 that has a receptacle 198 in its proximal end 200 for receiving a cable connector 202 of a cable 204. One or more wires 206 in communication with the wires in cable 204 extend from cable connector 202 or cable 204 to a support member 208 for supporting a kill switch 210. Support member 208 is a flexible substrate that can be positioned on or affixed to catheter handle 196, such as at proximal end 200. For example, flexible member 208 could be glued with a suitable sterile adhesive or tied or strapped to catheter handle 196.

Figure 14:
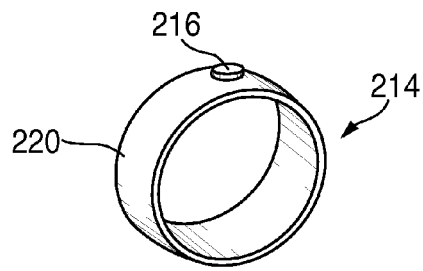
FIG. 14 is a schematic representation of on/off or kill switch that can be positioned on a catheter handle.

FIG. 14 is one embodiment of an on/off or kill switch that could be positioned on a catheter handle or elsewhere. Switching mechanism 214 comprises a button or switch 216 positioned on a flexible or semi-flexible substrate 220 that can be tied, strapped, adhered, or otherwise affixed to the distal end of a catheter handle (not shown) or other structure or location, such as a cabinet, table, or even the operator's person, such as a wrist. Substrate 220 comprises a power source and electronics to generate a signal, such as an inductive or other signal that will create impedance or otherwise will interrupt ablation therapy in an ablation catheter system. Alternatively, switch mechanism 214 may transmit a signal to a component that is connected to or in a cable transmitting ablation therapy where the component has a receiver for receiving the signal and a mechanical or electronic switch for interrupting the ablation therapy.

EXAMPLE

A standard ablation catheter and a depressible red kill switch was spliced into the main conductor leading to the distal ablation electrode. The switch was positioned on the ablation handle for immediate thumb control, and was reassembled so that all the steerable components functioned according to design specifications. The system was then tested in vitro utilizing raw chicken and a standard approved RF ablation system.

FIGS. 1A and 1B represent a radiofrequency ablation catheter system employing the kill switch on a standard handle, wherein, a standard ablation catheter was modified to include a red button as a kill switch. The system was tested multiple times and consistently created in vitro ablation lesions with precise manual control. Depressing the kill switch immediately terminated therapy delivery thereby preventing inadvertent radiofrequency delivery.

Conclusions: An ergonomic kill switch located in the thumb position on a standard ablation catheter handle provides a novel simple safety feature for rapid termination of inadvertent ablation therapy. This study demonstrated the ease of operation of this novel system with particularly utility during ablation procedures proximal to the normal conduction system (thereby minimizing the risk of inadvertent heart block).

While certain embodiments of the present invention have been illustrated and described, it will be clear that the present invention is not limited to these embodiments only. Numerous modifications, changes, variations, substitutions and equivalents will be apparent to those skilled in the art, without departing from the spirit and scope of the present invention, as described in the following claims.

I claim:

1. In an improved ablation catheter system comprising (i) a longitudinally extending ablation catheter to be operated by one or more principal catheter operators and having a proximal end and a distal end, (ii) a handle attached to the proximal end of the catheter, (iii) a mechanism at the distal end of the catheter for delivering ablation therapy to a desired location, and (iv) an ablation therapy generator or controller in communication with the handle and the distal end of the catheter, the improvement wherein the ablation catheter system comprises a manually operated switching mechanism operated by a principal catheter operator and positioned between the distal end of the catheter and the ablation therapy generator or controller and which is capable of causing abrupt disruption and termination of ablation therapy, whereupon the switching mechanism resets following ablation therapy termination and the ablation therapy generator or controller must be manually re-initiated to apply or continue ablation therapy.

2. The ablation catheter system of claim 1, wherein the ablation is used for cardiac catheter ablation.

3. The ablation catheter system of claim 1, wherein the switching mechanism is a kill switch.

4. The ablation catheter system of claim 1, wherein the switching mechanism is interposed on or in communication with one or more conductor wires contained within (1) the ablation catheter, (2) an electrical connector cable, (3) a separate device connected between the catheter and the ablation therapy generator or controller, or (4) the ablation therapy generator or controller.

5. The ablation catheter system of claim 1, wherein the switching mechanism is contained on or within the catheter handle, which is in or in communication with a connector cable or a separate device connected between the catheter and the ablation therapy generator or controller.

6. The ablation catheter system of claim 1, wherein the location of the switching mechanism permits easy and direct manual access by a principal catheter operator to immediately and abruptly terminate therapy.

7. The ablation catheter system of claim 1, wherein the switching mechanism is contained on or within the handle, which is in or in communication with a connector cable or the ablation therapy generator or controller.

8. The ablation catheter system of claim 1, wherein the switching mechanism comprises wires, connectors, a switch, and a protective enclosure to permit operation on a sterile medical field.

9. The ablation catheter system of claim 1, wherein the switching mechanism is placed in an ergonomic position on the handle in an easily accessible position to provide immediate manual control by a principal catheter operator to terminate therapy.

10. The ablation catheter system of claim 1, wherein the switching mechanism is within reach of a principal catheter operator to permit the principal catheter operator to manually perform an ablation procedure and to manually terminate therapy while maintaining sterility.

11. The ablation catheter system of claim 1, wherein the switching mechanism is controlled remotely, wired, or wirelessly, to immediately and abruptly terminate therapy.

12. The ablation catheter system of claim 11, wherein the switching mechanism is located on a remote control or remote controller, handle controller, computer controller, or joy stick to remotely control delivery of therapy.

13. The ablation catheter system of claim 12, wherein the remote controller, handle controller, computer controller, or joy stick has one or more other control functions to remotely manipulate the ablation catheter system.

14. The ablation catheter system of claim 1, wherein the switching mechanism is voice-, touch-, or sound-activated and is coupled either directly or remotely to the ablation therapy delivery system.

15. The ablation system of claim 1, wherein the switching mechanism is capable of controlling, disrupting, or controlling and disrupting at least one surveillance signal necessary to provide ablation therapy, thereby terminating therapy delivery.

16. The ablation system of claim 15, wherein the ablation therapy is cryoablation or another non-electrical ablation modality.

17. The ablation system of claim 1, wherein the switching mechanism comprises circuitry in which ablation therapy delivery can be immediately disrupted without interrupting any of the system's other functions or electrical capabilities.

18. The system of claim 1, in which haptics are coupled to the handle to provide feedback to a principal catheter operator regarding the amount of contact pressure or contact force that is being delivered at the end or ends of the ablation catheter system as it makes contact with structures or tissues within the human body.

19. The system of claim 1, which further comprises an automatic sensor to sense early signs of inadvertent therapy selected from the group consisting of phrenic nerve injury, perforation, and damage to the conduction system and is capable of sending a signal to the switching mechanism to immediately cease therapy delivery.

20. The system of claim 1, wherein a switching mechanism for use with an ablation catheter system comprises:
    a first wired or wireless component for direct manual activation, which is capable of being attached to or placed adjacent to an ablation catheter handle, and
    a second wired or wireless component coupled to the first component to receive, transmit, or receive and transmit a switching signal generated by the first component, to provide direct manual control of the delivery of ablation therapy.

21. The system of claim 20, wherein the first component can be attached to the catheter handle with a sleeve, a stretchable sleeve, a clip, a connector, or sterile adhesive.

22. The system of claim 21, wherein a sleeve or stretchable sleeve is configured to fit over a catheter handle and provide enhanced grippability and/or comfort.

23. In an improved ablation catheter system comprising (i) a longitudinally extending catheter to be operated by at least one principal catheter operator and having a proximal end and a distal end, (ii) a handle attached to the proximal end of the catheter, (iii) a mechanism at the distal end of the catheter for delivering ablation therapy to tissue, and (iv) a source of ablation therapy in communication with the handle and the distal end of the catheter,
    the improvement wherein the system has a manually operated switching mechanism positioned between the catheter and a therapy generating generator or controller and operated by a principal catheter operator to abruptly disrupt and terminate therapy and one or more additional safety features to minimize the risk of inadvertent damage to tissue, whereupon the switching mechanism resets following ablation therapy termination and the ablation therapy generator or controller must be manually re-initiated to apply or continue ablation therapy.

24. The system of claim 23, wherein shock absorbing materials are interposed between the distal end of the catheter and the catheter to help absorb contact force and minimize pressure delivered to the tissue and the risk of inadvertent damage to the tissue.

25. The system of claim 23, wherein one or more contact pressure or contact force sensors to detect and minimize excessive force delivered to a distal end of an ablation catheter system are interposed between the ablation therapy delivery end or ends and the catheter to monitor, control, or monitor and control the degree of contact pressure or contact force applied to the tissue to prevent injury to the tissue.

26. In an improved ablation catheter system comprising (i) a longitudinally extending ablation catheter to be operated by one or more principal catheter operators and having a proximal end and a distal end, (ii) a handle attached to the proximal end of the catheter, (iii) a mechanism at the distal end of the catheter for delivering ablation therapy to a desired location, and (iv) an ablation therapy generator or controller in communication with the handle and the distal end of the catheter, the improvement wherein the ablation catheter system comprises a manually operated switching mechanism operated by a principal catheter operator and positioned on or within the catheter handle and which is capable of causing abrupt disruption and termination of ablation therapy, whereupon the switching mechanism resets following ablation therapy termination and the ablation therapy generator or controller must be manually re-initiated to apply or continue ablation therapy.

27. The ablation catheter system of claim 26, wherein the switching mechanism is placed in an ergonomic position on the handle in an easily accessible position to provide immediate manual control by a principal catheter operator to terminate therapy.

\* \* \* \* \*